(12) United States Patent
Martyres et al.

(10) Patent No.: US 7,718,654 B2
(45) Date of Patent: May 18, 2010

(54) SUBSTITUTED PTERIDINES FOR THE TREATMENT OF INFLAMMATORY DISEASES

(75) Inventors: Domnic Martyres, Biberach (DE); Horst Dollinger, Schemmerhofen (DE); Birgit Jung, Laupheim (DE); Peter Nickolaus, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 85 days.

(21) Appl. No.: 11/282,161

(22) Filed: Nov. 18, 2005

(65) Prior Publication Data

US 2006/0116371 A1 Jun. 1, 2006

(30) Foreign Application Priority Data

Nov. 29, 2004 (DE) ........................ 10 2004 057 645

(51) Int. Cl.
- C07D 475/08 (2006.01)
- C07D 413/14 (2006.01)
- A61K 31/4985 (2006.01)
- A61K 31/5355 (2006.01)
- A61P 35/00 (2006.01)
- A61P 29/00 (2006.01)
- A61P 11/00 (2006.01)
- A61P 25/00 (2006.01)

(52) U.S. Cl. .................. 514/234.2; 514/248; 544/260; 544/118

(58) Field of Classification Search ............... 544/257, 544/258, 259, 260, 118; 514/250, 248, 234.5
See application file for complete search history.

(56) References Cited

U.S. PATENT DOCUMENTS

| | | | |
|---|---|---|---|
| 2,940,972 | A | 6/1960 | Roth |
| 4,560,685 | A | 12/1985 | Roch et al. |
| 7,205,408 | B2 | 4/2007 | Davies |
| 2005/0054653 | A1 | 3/2005 | Eisenbrand et al. |
| 2006/0116370 | A1 | 6/2006 | Dollinger et al. |
| 2006/0116372 | A1 | 6/2006 | Dollinger et al. |
| 2006/0116373 | A1 | 6/2006 | Dollinger et al. |

FOREIGN PATENT DOCUMENTS

| | | |
|---|---|---|
| CA | 1233179 | 2/1988 |
| CA | 1252783 | 4/1989 |
| CA | 1337813 | 12/1995 |
| DE | 3323932 A1 | 10/1985 |
| DE | 3445298 | 6/1986 |
| DE | 3540952 | 5/1987 |
| EP | 0134922 | 3/1985 |
| EP | 0185259 A2 | 6/1986 |
| GB | 2143232 A | 2/1985 |
| WO | WO/00/39129 * | 7/2000 |
| WO | 2003062240 A1 | 7/2003 |
| WO | WO03062240 | 7/2003 |

OTHER PUBLICATIONS

European Respiratory Society, Feb. 13, 2007, http://www.newtocopd.com/currentaffairsnews/list751_item17680.aspx, downloaded Jan. 16, 2008.*
Implications for Rheumatoid Arthritis <http://www.medscape.com/viewarticle/464104>, downloaded Jan. 17, 2008.*
Targan, et al., Inflammatory Bowel Disease: From Bench to Bedside, 2nd Edition, pp. 553-571, 2003.*
Prehn, et al., J. Clin. Immunol., vol. 21, No. 5, 2001, pp. 357-364.*
Merz, et al; Synthesis of 7-Benzylamino-6-chloro-2-piperazino-4-pyrrolidinopteridine and Novel Derivatives Free of Positional Isomers. Potent Inhibitors of cAMP-Specific Phosphodiesterase and of Malignant Tumor Cell Growth; Journal of Medicinal Chemistry, American Chemical Society; 1998; vol. 41 (24); pp. 4733-4743.
Doherty; Phosphodiesterase 4 inhibitors as novel anti-inflammatory agents; Current Opinion in Chemical Biology; 1999; No. 3, pp. 466-473.
Yamamoto, K.A et al.; "Differential activity of drugs to induce emesis and pica behavior in *Suncus murinus* (house musk shrew) and rats", Physiology & Behavior, 2004, pp. 151-156, 83.

* cited by examiner

Primary Examiner—James O Wilson
Assistant Examiner—Cecilia M Jaisle
(74) Attorney, Agent, or Firm—Michael P. Morris; Mary-Ellen M. Devlin; Alan R. Stempel

(57) ABSTRACT

The invention relates to new pteridine compounds of formula 1

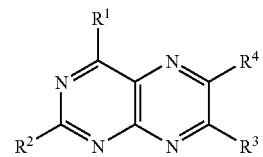

wherein $R^1$, $R^2$, $R^3$ and $R^4$ have the meanings given herein, which are useful for the treatment of respiratory or gastrointestinal complaints or diseases, inflammatory diseases of the joints, skin or eyes, diseases of the peripheral or central nervous system, or cancers. The invention further relates to pharmaceutical compositions which contain these compounds.

7 Claims, No Drawings

SUBSTITUTED PTERIDINES FOR THE TREATMENT OF INFLAMMATORY DISEASES

The invention relates to new pteridines which are suitable for the treatment of
respiratory or gastrointestinal complaints or diseases,
inflammatory diseases of the joints, skin or eyes,
diseases of the peripheral or central nervous system or cancers, as well as pharmaceutical compositions which contain these compounds.

PRIOR ART

Pteridines are known from the prior art as active substances with an antiproliferative activity. Merz et al. describe in the Journal of Medicinal Chemistry 1998, 41, 4733-4743 the preparation of 7-benzylamino-6-chloro-2-piperazino-4-pyrrolidinopteridine and derivatives thereof which are free from positional isomers. It has been shown that the compounds prepared are able to inhibit the growth of tumour cells. DE 3540952 describes 2-piperazino-pteridines which are substituted in the 6 position by a halogen atom, selected from among fluorine, chlorine or bromine. It has been shown that these compounds were able to inhibit the activity of tumour cells and human thrombocytes in vitro. DE 3323932 discloses 2-piperazino-pteridines which carry a dialkylamino, piperidino, morpholino, thiomorpholino or 1-oxidothiomorpholino group in the 4 position. It has been shown that these compounds were able to inhibit the activity of tumour cells and human thrombocytes in vitro. DE 3445298 describes pteridines with a large number of different substituents in the 2, 4, 6 and 7 position, while compounds with a 2-piperazino group on the pteridine skeleton are suitable as inhibitors of tumour growth as well as having antithrombotic and metastasis-inhibiting properties. U.S. Pat. No. 2,940,972 discloses tri- and tetrasubstituted pteridine derivatives, while general statements are made to the effect that these pteridines have valuable pharmacological properties, namely coronary-dilatory, sedative, antipyretic and analgesic effects.

The phosphodiesterase 4 inhibitors known from the prior art are known to trigger side effects such as nausea and vomiting (Doherty, 1999, Curr. Op. Chem. Biol., Aug. 3, (4):466-73). The substances mentioned in this invention are particularly preferably suitable for the treatment of the above-mentioned diseases, as they did not cause these side effects in an animal model for nausea and vomiting (S. Murinus, Yamamoto K. et al., Physiol. Behav., 2004, Oct. 30, 83(1), 151-6).

The aim of the present invention is to provide new compounds which are suitable for the prevention or treatment of respiratory or gastrointestinal complaints or diseases, inflammatory diseases of the joints, skin or eyes, diseases of the peripheral or central nervous system, or cancers, particularly those compounds which are characterised by reduced side effects, particularly emesis and nausea.

DESCRIPTION OF THE INVENTION

Surprisingly it has now been found that pteridines of formula 1 are suitable for the treatment of inflammatory diseases. The present invention therefore relates to compounds of formula 1

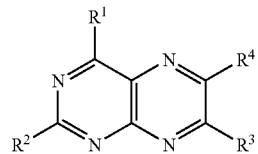

wherein
$R^1$ denotes a heterocyclic ring which contains a nitrogen atom;
$R^2$ denotes halogen, $OR^{2.1}$, $SR^{2.1}$, $NR^{2.1}R^{2.2}$ or a group selected from among aryl, het and hetaryl, optionally substituted by a group selected from among $C_{1-6}$-alkyl, $O-C_{1-6}$-alkyl, $C_{3-6}$-cycloalkyl, $C_{7-11}$-aralkyl and $N(C_{1-4}$-alkyl$)_2$;
$R^{2.1}$ denotes H, $C_{1-4}$-alkyl, aryl, $C_{7-11}$-aralkyl;
$R^{2.2}$ denotes H, $C_{1-4}$-alkyl, aryl, $C_{7-11}$-aralkyl;
$R^3$ denotes aryl, het, hetaryl or a group of formula 1a,

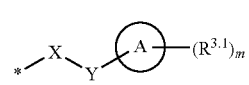

wherein
A denotes aryl, hetaryl;
X denotes $NR^{3.2}$, S, O;
Y denotes $C_{1-4}$-alkylene, optionally substituted by one or more $R^{3.3}$
m denotes 0, 1, 2, 3;
$R^{3.1}$ each independently of one another denote $C_{1-6}$-alkyl, $C_{1-6}$-haloalkyl, $C_{1-6}$-alkyl-$CONR^{3.1.1}R^{3.1.2}$, $-C_{1-6}$-alkyl-$NR^{3.1.1}R^{3.1.2}$, $OR^{3.1.1}$, $O-C_{1-6}$-haloalky, $NHCOR^{3.1.1}$, $SO_2R^{3.1.1}$, aryl, halogen, CN, OH, $CONR^{3.1.1}R^{3.1.2}$; or
$R^{3.1}$ together with two atoms of A forms a 5- or 6-membered carbocyclic ring or a 5- or 6-membered heterocyclic ring which may contain one or more oxygen or nitrogen atoms;
$R^{3.1.1}$ denotes H, $C_{1-6}$-alkyl,
$R^{3.1.2}$ denotes H, $C_{1-6}$-alkyl,
$R^{3.2}$ denotes H, $C_{1-6}$-alkyl;
$R^{3.3}$ each independently of one another denote $C_{1-6}$-alkyl, $C_{1-6}$-alkyl-OH, $C_{3-6}$-cycloalkyl-OH, $COOR^{3.3.1}$, $CONR^{3.3.1}R^{3.3.2}$; or
$R^{3.3}$ together with one or two carbon atoms of Y forms a carbocyclic ring with 3, 4, 5 or 6 carbon atoms
$R^{3.3.1}$ denotes H, $C_{1-6}$-alkyl;
$R^{3.3.2}$ denotes H, $C_{1-6}$-alkyl;
$R^4$ denotes a group selected from among $C_{1-6}$-alkyl, $C_{2-6}$-alkenyl, $C_{2-6}$-alkynyl, $C_{3-6}$-cycloalkyl, $C_{3-6}$-cycloalkenyl, $OR^{4.1}$, $SR^{4.1}$, $C_{1-6}$-haloalkyl, $NR^{4.1}R^{4.2}$ or a group selected from among aryl, het and hetaryl, optionally substituted by one or more groups selected from among $C_{1-6}$-alkyl, $C_{1-6}$-haloalkyl, CN, $O-C_{1-6}$-alkyl, halogen,
$R^{4.1}$ denotes H, $C_{1-6}$-alkyl, aryl, $C_{7-11}$-aralkyl;
$R^{4.2}$ denotes H, $C_{1-6}$-alkyl, aryl, $C_{7-11}$-aralkyl;

and the pharmacologically acceptable salt, diastereomers, enantiomers, racemates, hydrates or solvates thereof.

Preferred compounds of formula 1 above are those wherein
$R^1$ denotes a heterocyclic ring which contains a nitrogen atom;

$R^2$ denotes halogen, $OR^{2.1}$, $SR^{2.1}$, $NR^{2.1}R^{2.2}$ or a group selected from among aryl, het and hetaryl, optionally substituted by a group selected from among $C_{1-6}$-alkyl, $O-C_{1-6}$-alkyl, $C_{3-6}$-cycloalkyl, $C_{7-11}$-aralkyl and $N(C_{1-4}$-alkyl$)_2$;

$R^{2.1}$ denotes $C_{1-4}$-alkyl, aryl, $C_{7-11}$-aralkyl;

$R^{2.2}$ denotes H, $C_{1-4}$-alkyl;

$R^3$ denotes aryl, het, hetaryl or a group of formula 1a,

wherein
A denotes aryl, hetaryl;
X denotes $NR^{3.2}$, S, O;
Y denotes $C_{1-4}$-alkylene, optionally substituted by one or more $R^{3.3}$
m denotes 0, 1, 2;
$R^{3.1}$ each independently of one another denote $C_{1-6}$-alkyl, $C_{1-6}$-haloalkyl, $C_{1-6}$-alkyl-$CONH_2$, —$C_{1-6}$-alkyl-$NH_2$, $O-C_{1-6}$-alkyl, $O-C_{1-6}$-haloalkyl, $NHCO-C_{1-6}$-alkyl, $SO_2-C_{1-6}$-alkyl, aryl, halogen, CN, OH, $CONH_2$; or
$R^{3.1}$ together with two atoms of A forms a 5- or 6-membered carbocyclic ring or a 5- or 6-membered heterocyclic ring which may contain one or more oxygen or nitrogen atoms;
$R^{3.2}$ denotes H, $C_{1-6}$-alkyl;
$R^{3.3}$ each independently of one another denote $C_{1-6}$-alkyl, $C_{1-6}$-alkyl-OH, $C_{3-6}$-cycloalkyl-OH, $COO-C_{1-6}$-alkyl, COOH, $CONH_2$; or
$R^{3.3}$ together with one or two carbon atoms of Y forms a carbocyclic ring with 3, 5 or 6 carbon atoms
$R^4$ denotes a group selected from among $C_{1-6}$-alkyl, $C_{2-6}$-alkenyl, $C_{2-4}$-alkynyl, $C_{3-6}$-cycloalkyl, $C_{3-6}$-cycloalkenyl, $O-C_{1-6}$alkyl, $S-C_{1-6}$-alkyl, $C_{1-6}$-haloalkyl, $NR^{4.1}R^{4.2}$ or a group selected from among aryl, het and hetaryl, optionally substituted by one or more groups selected from among $C_{1-6}$-alkyl, $C_{1-6}$-haloalkyl, CN, $O-C_{1-6}$-alkyl, halogen,
$R^{4.1}$ denotes H, $C_{1-6}$-alkyl;
$R^{4.2}$ denotes $C_{1-6}$-alkyl, aryl;

and pharmacologically acceptable salt, diastereomers, enantiomers, racemates, hydrates or solvates thereof.

Preferred compounds of formula 1 above are those wherein
$R^4$ denotes $C_{3-6}$-cycloalkyl, preferably cyclopropyl;

and the pharmacologically acceptable salt, diastereomers, enantiomers, racemates, hydrates or solvates thereof. Of these, preferred compounds of formula 1 are those wherein
$R^3$ denotes a group of formula 1a,

wherein
A denotes aryl, hetaryl;
X denotes $NR^{3.2}$, S, O;
Y denotes $C_{1-4}$-alkylene, optionally substituted by one or more $R^{3.3}$
m denotes 0, 1, 2;

$R^{3.1}$ each independently of one another denote $C_{1-4}$-alkyl, $C_{1-4}$-haloalkyl, $C_{1-4}$-alkyl-$CONH_2$, —$C_{1-4}$-alkyl-$NH_2$, $O-C_{1-4}$-alkyl, $O-C_{1-4}$-haloalkyl, $NHCO-C_{1-4}$-alkyl, $SO_2-C_{1-4}$-alkyl, aryl, halogen, CN, OH, $CONH_2$; or
$R^{3.1}$ together with two atoms of A forms a 5- or 6-membered carbocyclic ring or a 5- or 6-membered heterocyclic ring which may contain one or more oxygen or nitrogen atoms;
$R^{3.2}$ denotes H, $C_{1-4}$-alkyl;
$R^{3.3}$ each independently of one another denote $C_{1-4}$-alkyl, $C_{1-4}$-alkyl-OH, $C_{3-4}$-cycloalkyl-OH, $COO-C_{1-4}$-alkyl, COOH, $CONH_2$; or
$R^{3.3}$ together with one or two carbon atoms of Y forms a carbocyclic ring with 3, 5 or 6 carbon atoms and the pharmacologically acceptable salt, diastereomers, enantiomers, racemates, hydrates or solvates thereof. Of these, particularly preferred compounds of formula 1 are those wherein
$R^3$ denotes a group of formula 1a, wherein
A denotes aryl, hetaryl;
X denotes NH, S, O;
Y denotes $C_{1-4}$-alkylene, optionally substituted by one or more $R^{3.3}$
m denotes 0, 1, 2;
$R^{3.1}$ each independently of one another denote $C_{1-4}$-alkyl, $C_{1-4}$-haloalkyl, $C_{1-4}$-alkyl-$CONH_2$, $C_{1-4}$-alkyl-$NH_2$, $O-C_{1-4}$-alkyl, $O-C_{1-4}$-haloalkyl, $NHCO-C_{1-4}$-alkyl, $SO_2-C_{1-4}$-alkyl, halogen, CN, OH, $CONH_2$;
$R^{3.3}$ each independently of one another denote $C_{1-4}$-alkyl, $C_{1-4}$-alkyl-OH, $C_{3-4}$-cycloalkyl-OH, $COO-C_{1-4}$-alkyl, COOH, $CONH_2$; or
$R^{3.3}$ together with one or two carbon atoms of Y forms a carbocyclic ring with 3, 5 or 6 carbon atoms and the pharmacologically acceptable salt, diastereomers, enantiomers, racemates, hydrates or solvates thereof. Most preferred of these are the above compounds of formula 1, wherein
$R^3$ denotes a group of formula 1a, wherein
A denotes aryl, hetaryl;
X denotes NH, S, O;
Y denotes $C_{1-4}$-alkylene, optionally substituted by one or two $R^{3.3}$;
m denotes 0, 1, 2;
$R^{3.1}$ each independently of one another denote $C_{1-4}$-alkyl, $C_{1-4}$-haloalkyl, $O-C_{1-4}$-alkyl, $O-C_{1-4}$-haloalkyl, halogen, CN, OH;
$R^{3.3}$ each independently of one another denote $C_{1-4}$-alkyl, COOH, $CONH_2$; or
$R^{3.3}$ together with one or two carbon atoms of Y forms a carbocyclic ring with 3 carbon atoms and the pharmacologically acceptable salt, diastereomers, enantiomers, racemates, hydrates or solvates thereof.

Also preferred are the above compounds of formula 1, wherein $R^2$ denotes halogen, $NR^{2.1}R^{2.2}$, het, optionally substituted by a group selected from among $C_{3-6}$-cycloalkyl, $C_{7-11}$-aralkyl and $NMe_2$;

$R^{2.1}$ denotes $C_{7-11}$-aralkyl;

$R^{2.2}$ denotes H;

$R^3$ denotes $NR^{3.1}R^{3.2}$, $SR^{3.1}$ or het;

$R^{3.1}$ denotes $C_{1-6}$-alkylene-$C_{3-6}$-cycloalkyl or $C_{7-11}$-aralkyl, optionally substituted by a group selected from the group halogen;

$R^{3.2}$ denotes H;

$R^4$ denotes a group selected from among $C_{1-6}$-alkyl, $C_{3-6}$-cycloalkyl, O—$C_{1-6}$-alkyl, $C_{1-6}$-haloalkyl, $NR^{4.1}R^{4.2}$ or a group selected from among aryl, het and hetaryl, optionally substituted by one or more groups selected from among $C_{1-6}$-alkyl, $C_{1-6}$-haloalkyl, CN, O—$C_{1-6}$-alkyl, halogen, $R^{4.1}$ denotes H, $C_{1-6}$-alkyl;

$R^{4.2}$ denotes $C_{1-6}$-alkyl, aryl;

and pharmacologically acceptable salt, diastereomers, enantiomers, racemates, hydrates or solvates thereof.

Particularly preferred are the above compounds of formula 1, wherein $R^2$ denotes halogen, $NR^{2.1}R^{2.2}$, het, optionally substituted by a group selected from among $C_{3-6}$-cycloalkyl, $C_{7-11}$-aralkyl and $NMe_2$;

$R^{2.1}$ denotes $C_{7-11}$-aralkyl;

$R^{2.2}$ denotes H;

$R^3$ denotes $NR^{3.1}R^{3.2}$, $SR^{3.1}$ or het;

$R^{3.1}$ denotes $C_{1-4}$-alkylene-$C_{3-6}$-cycloalkyl or $C_{7-11}$-aralkyl, optionally substituted by a group selected from the group halogen;

$R^{3.2}$ denotes H;

$R^4$ denotes a group selected from among $C_{1-4}$-alkyl, $C_{3-6}$-cycloalkyl, O—$C_{1-4}$-alkyl, $C_{1-4}$-haloalkyl, $NR^{4.1}R^{4.2}$, het, hetaryl, aryl, optionally substituted by one or more groups selected from among $C_{1-4}$-alkyl, $C_{1-4}$-haloalkyl, CN, O—$C_{1-4}$-alkyl, halogen, $R^{4.1}$ denotes H, $C_{1-4}$-alkyl;

$R^{4.2}$ denotes $C_{1-4}$-alkyl, aryl;

and pharmacologically acceptable salt, diastereomers, enantiomers, racemates, hydrates or solvates thereof.

Most preferred are the above compounds of formula 1, wherein $R^2$ denotes halogen, NH(benzyl), het, optionally substituted by a group selected from among cyclopropyl, benzyl and $NMe_2$;

$R^3$ denotes $NR^{3.1}R^{3.2}$, $SR^{3.1}$ or het;

$R^{3.1}$ denotes methylcyclohexyl or benzyl, optionally substituted by a group selected from among fluorine and chlorine;

$R^{3.2}$ denotes H;

$R^4$ denotes a group selected from among methyl, ethyl, propyl, 2-methylpropyl, cyclopropyl, cyclohexyl, methoxy, $CF_3$, $NR^{4.1}R^{4.2}$, het, hetaryl, aryl, optionally substituted by one or more groups selected from among methyl, $CF_3$, CN, methoxy, fluorine, chlorine, $R^{4.1}$ denotes H, methyl, ethyl;

$R^{4.2}$ denotes methyl, ethyl, phenyl;

and pharmacologically acceptable salt, diastereomers, enantiomers, racemates, hydrates or solvates thereof.

Particularly preferred are the above compounds of formula 1, wherein $R^1$ denotes a five- or six-membered heterocyclic ring which contains a nitrogen atom;

$R^2$ denotes chlorine, NH(benzyl), a six-membered heterocyclic ring which may contain one or more nitrogen atoms and is optionally substituted by a group selected from among cyclopropyl, benzyl and $NMe_2$;

$R^3$ denotes $NR^{3.1}R^{3.2}$, $SR^{3.1}$ or a six-membered heterocyclic ring which may contain one or more heteroatoms selected from among nitrogen and oxygen;

$R^{3.1}$ denotes methylcyclohexyl or benzyl, optionally substituted by a group selected from among fluorine and chlorine;

$R^{3.2}$ denotes H;

$R^4$ denotes a group selected from among methyl, ethyl, propyl, 2-methylpropyl, cyclopropyl, cyclohexyl, methoxy, $CF_3$, $NR^{4.1}R^{4.2}$, aryl, optionally substituted by one or more groups selected from among methyl, $CF_3$, CN, methoxy, fluorine, chlorine, a five- or six-membered heterocyclic ring which may contain one or more heteroatoms selected from among nitrogen and oxygen, a five-membered heterocyclic aromatic group which may contain one or more groups selected from among nitrogen and oxygen, an aromatic or non-aromatic bicyclic group which may contain one or more heteroatoms selected from among sulphur and oxygen;

$R^{4.1}$ denotes H, methyl, ethyl;

$R^{4.2}$ denotes methyl, ethyl, phenyl;

and pharmacologically acceptable salt, diastereomers, enantiomers, racemates, hydrates or solvates thereof.

Most particularly preferred are the above compounds of formula 1, wherein $R^1$ denotes a group selected from among

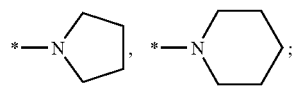

$R^2$ denotes a group selected from among chlorine,

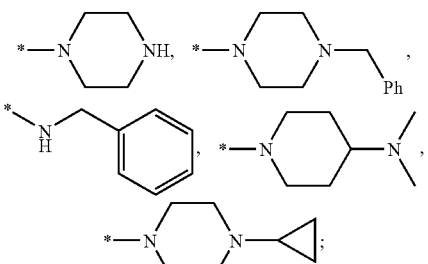

$R^3$ denotes a group selected from among

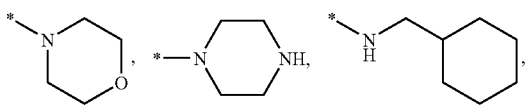

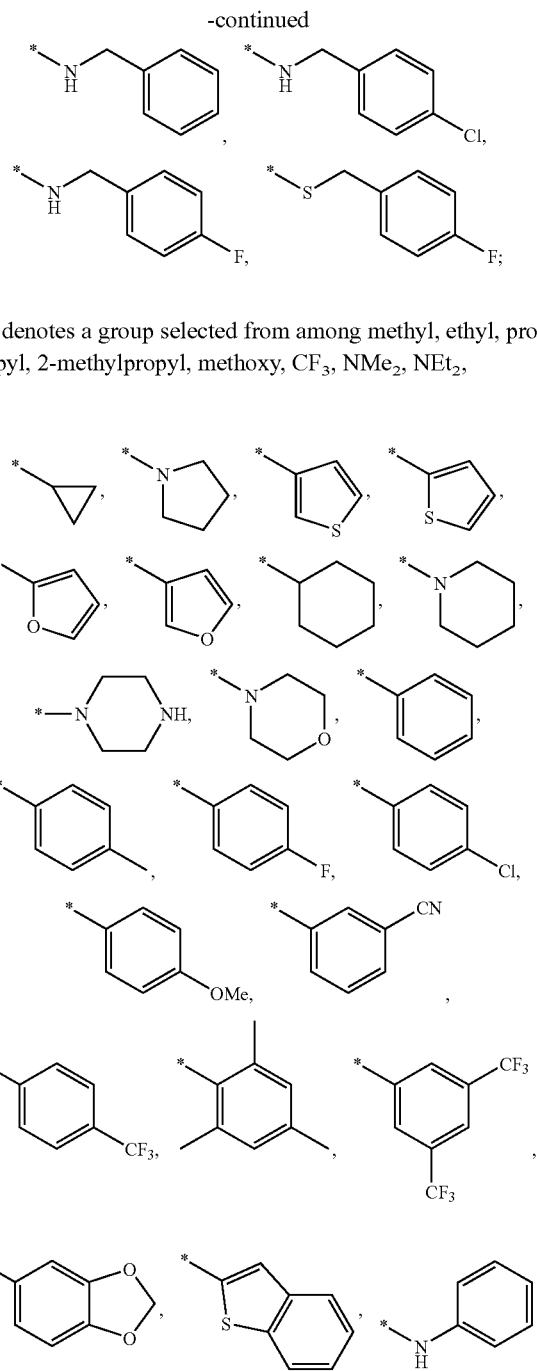

$R^4$ denotes a group selected from among methyl, ethyl, propyl, 2-methylpropyl, methoxy, $CF_3$, $NMe_2$, $NEt_2$, and pharmacologically acceptable salt, diastereomers, enantiomers, racemates, hydrates or solvates thereof.

Terms and Definitions Used

Within the scope of this application, when defining possible substituents, these may also be shown in the form of a structural formula. An asterisk (*) in the structural formula of the substituent is construed as the binding site to the rest of the molecule. Thus, for example, the groups N-piperidinyl (I), 4-piperidinyl (II), 2-tolyl (III), 3-tolyl (IV) and 4-tolyl (V) are shown as follows:

If there is no asterisk (*) in the structural formula of the substituent, each hydrogen atom may be removed from the substituent and the valency thus liberated may serve as a binding site to the rest of a molecule. Thus, for example, VI may represent 2-tolyl, 3-tolyl, 4-tolyl and benzyl.

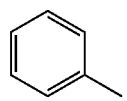

By pharmacologically acceptable acid addition salts are meant for example those salts which are selected from among hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

By the term "$C_{1-6}$-alkyl" (including those which are part of other groups) are meant branched and unbranched alkyl groups with 1 to 6 carbon atoms and by the term "$C_{1-4}$-alkyl" are meant branched and unbranched alkyl groups with 1 to 4 carbon atoms. Alkyl groups with 1 to 4 carbon atoms are preferred. Examples include: methyl, ethyl, n-propyl, iso-propyl, n-butyl, iso-butyl, sec-butyl, tert-butyl, n-pentyl, iso-pentyl, neo-pentyl or hexyl. The following abbreviations may optionally also be used for the above-mentioned groups: Me, Et, n-Pr, i-Pr, n-Bu, i-Bu, t-Bu, etc. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl, or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl or hexynyl. Unless stated otherwise, the definitions propynyl, butynyl, pentynyl and hexynyl include all the possible isomeric forms of the groups in question. Thus, for example, propynyl includes 1-propynyl and 2-propynyl, butynyl includes 1-, 2- and 3-butynyl, 1-methyl-1-propynyl, 1-methyl-2-propynyl etc.

By the term "$C_{1-4}$-alkylene" (including those which are part of other groups) are meant branched and unbranched alkylene groups with 1 to 4 carbon atoms. Examples include: methylene, ethylene, propylene, 1-methylethylene, butylene, 1-methylpropylene, 1,1-dimethylethylene or 1,2-dimethylethylene. Unless stated otherwise, the definitions propylene and butylene include all the possible isomeric forms of the groups in question with the same number of carbons. Thus, for example, propyl also includes 1-methylethylene and butylene includes 1-methylpropylene, 1,1-dimethylethylene, 1,2-dimethylethylene. If the carbon chain is substituted by a group which together with one or two carbon atoms of the alkylene chain forms a carbocyclic ring with 3, 4, 5 or 6 carbon atoms, the following are thus included as examples of the rings:

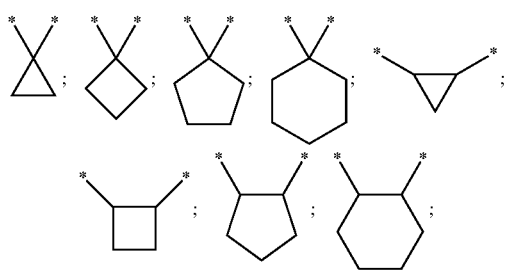

By the term "$C_{3-6}$-cycloalkyl" (including those which are part of other groups) are meant cyclic alkyl groups with 3 to 6 carbon atoms. Examples include: cyclopropyl, cyclobutyl, cyclopentyl or cyclohexyl. Unless otherwise statedd, the cyclic alkyl groups may be substituted by one or more groups selected from among methyl, ethyl, iso-propyl, tert-butyl, hydroxy, fluorine, chlorine, bromine and iodine.

By the term "$C_{7-11}$-aralkyl" (including those which are part of other groups) are meant branched and unbranched alkyl groups with 1 to 5 carbon atoms, which are substituted by an aromatic ring system having 6 carbon atoms. Examples include: benzyl, 1- or 2-phenylethyl. Unless otherwise stated, the aromatic groups may be substituted by one or more groups selected from among methyl, ethyl, iso-propyl, tert-butyl, hydroxy, fluorine, chlorine, bromine and iodine.

Halogen within the scope of the present invention denotes fluorine, chlorine, bromine or iodine. Unless stated to the contrary, fluorine, chlorine and bromine are regarded as preferred halogens.

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-alkyl" are meant branched and unbranched alkyl groups with 1 to 4 carbon atoms, which are substituted by one or more halogen atoms. Alkyl groups with 1 to 4 carbon atoms are preferred. Examples include: $CF_3$, $CHF_2$, $CH_2F$, $CH_2CF_3$.

By the term "aryl" (including those which are part of other groups) are meant aromatic ring systems with 6 or 10 carbon atoms. Examples include: phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

By the term "heterocyclic rings" or "het" are meant five-, six- or seven-membered, saturated or unsaturated heterocyclic rings or 5-10 membered, bicyclic heterorings which may contain one, two or three heteroatoms, selected from among oxygen, sulphur and nitrogen, while the ring may be linked to the molecule through a carbon atom or, if available, through a nitrogen atom. The following are examples of five-, six- or seven-membered, saturated or unsaturated heterocyclic rings:

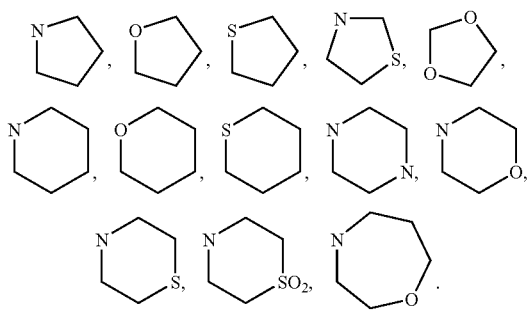

Unless otherwise mentioned, a heterocyclic ring may be provided with a keto group. Examples of this include.

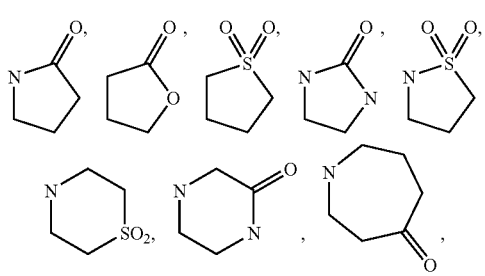

Examples of 5-10-membered bicyclic heterorings include pyrrolizine, indole, indolizine, isoindole, indazole, purine, quinoline, isoquinoline, benzimidazole, benzofuran, benzopyran, benzothiazole, benzothiazole, benzoisothiazole, pyridopyrimidine, pteridine, pyrimidopyrimidine,

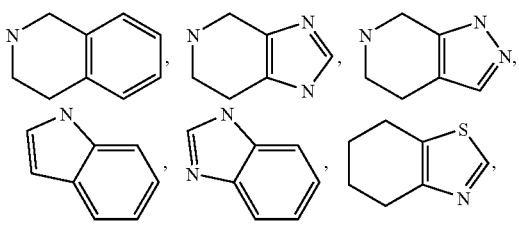

Although it is covered by the term "heterocyclic rings" or "het", the term "heterocyclic aromatic groups" or "hetaryl" denotes five- or six-membered heterocyclic aromatic groups or 5-10 membered, bicyclic heteroaryl rings which may contain one, two or three heteroatoms, selected from among oxygen, sulphur and nitrogen, and contain sufficient conjugated double bonds to form an aromatic system. The ring may be linked to the molecule through a carbon atom or if available through a nitrogen atom. Examples of five- or six-membered heterocyclic aromatic groups include:

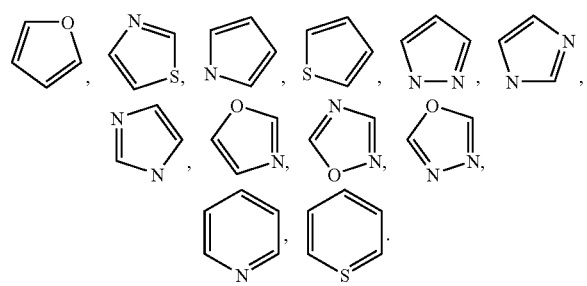

EXAMPLES

The following general methods may be used to synthesise the Examples listed in the Table that follows.

tert. butyl 4-(7-benzylamino-6-chloro-4-pyrrolidin-1-yl-pteridin-2-yl)-piperazine-1-carboxylate: 1.02 g (2.40 mmol) 7-benzylamino-6-chloro-2-piperazino-4-pyrrolidino-pteridine are placed in 10 ml of tetrahydrofuran, 1.05 g (4.80 mmol) BOC-anhydride and 5 ml saturated sodium hydrogen carbonate solution are added. The mixture is stirred for 1.5 hours at ambient temperature, then evaporated down in vacuo. The aqueous residue is diluted with water, the precipitate is suction filtered, washed and dried.

Yield: 1.17 g (=93% of theoretical)

Example 24

Benzyl-(6-methoxy-2-piperazin-1-yl-4-pyrrolidin-1-yl-pteridin-7-yl)-amine: 100 mg (1.76 mmol) sodium methoxide and 300 mg (0.571 mmol) tert.butyl 4-(7-benzylamino-6-chloro-4-pyrrolidin-1-yl-pteridin-2-yl)-piperazine-1-carboxylate are suspended in 5 ml of tetrahydrofuran, then placed in the microwave for 0.1 hours at 120° C. Then the reaction mixture is concentrated by evaporation, the residue is combined with methanol and suction filtered. The mother liquor is concentrated by evaporation, then extracted with water and dichloromethane. The organic phase is dried and evaporated to dryness. The residue is purified by chromatography. Corresponding fractions are concentrated by evaporation and crystallised from diethyl ether.

Yield: 40 mg (=13% of theoretical)

The following general methods A, B, C, or D may be used to synthesise the Examples listed in the Table (see below):

A) Synthesis of Examples 1, 2, 3, 23 and 30

500 mg (0.952 mmol) tert.butyl 4-(7-benzylamino-6-chloro-4-pyrrolidin-1-yl-pteridin-2-yl)-piperazine-1-carboxylate are placed under an $N_2$ atmosphere, then 19.0 mg (0.0540 mmol) iron-(III)-acetylacetonate and 0.50 ml N-methylpyrrolidone are added. While cooling with ice 1.45 ml (2.90 mmol) 2 M isobutylmagnesium bromide solution in diethyl ether are added dropwise. The mixture is stirred for 1 hour at ambient temperature. Then 30 ml of water are added, and the mixture is combined with ethyl acetate. The resulting emulsion is filtered, then the phases are separated. The organic phase is washed with saturated sodium chloride solution, dried and evaporated to dryness. The residue is purified by chromatography.

Yield: 470 mg (=90% of theoretical)

The representative cleaving method E was then used to synthesise Examples 1, 2, 3, 23, 30.

B) Synthesis of Examples 4, 5, 6, 7, 8, 9, 10, 11, 12, 14, 15, 16, 17, 18, 20 and 22

500 mg (0.952 mmol) tert.butyl 4-(7-benzylamino-6-chloro-4-pyrrolidin-1-yl-pteridin-2-yl)-piperazine-1-carboxylate, 122 mg (0.952 mmol) 2-thiopheneboric acid and 203 mg (1.915 mmol) sodium carbonate are placed in 5 ml of toluene, 1 ml of ethanol and 1 ml of water, then heated to 80° C. At this temperature 50 mg (0.0680 mmol) [1,1'-bis(diphenyl-phosphino)ferrocene]palladium(II)chloride are added, then the mixture is stirred for 16 hours. Then the reaction mixture is extracted with water and dichloromethane, the aqueous phase is separated off using a separating cartridge and the organic phase is evaporated to dryness. The residue is purified by chromatography.

Yield: 504 mg (=92% of theoretical).

The representative cleaving method E was then used to synthesise Examples 4, 5, 6, 7, 8, 9, 10, 11, 12, 14, 15, 16, 17, 18, 20, 22.

C) Synthesis of Examples 13, 19, 21 and 25

800 mg (1.524 mmol) tert.butyl 4-(7-benzylamino-6-chloro-4-pyrrolidin-1-yl-pteridin-2-yl)-piperazine-1-carboxylate, 0.15 ml (1.828 mmol) pyrrolidine, 28 mg (0.0310 mmol) tris(dibenzylideneacetone)-dipalladium(0), 29 mg (0.0610 mmol) 2-dicyclohexylphosphino-2'4'6'-tri-iso-propyl-11'- biphenyl and 205 mg (2.133 mol) sodium-tert.-butoxide are placed in 3 ml of toluene, then stirred for 80 hours at 100° C. Then the reaction mixture is extracted with water and ethyl acetate. The organic phase is separated off and dried, then applied to Extrelut and purified by chromatography. The corresponding fractions are evaporated to dryness, the residue is combined with dichloromethane and 1 ml trifluoromethylacetic acid is added. The mixture is stirred at ambient temperature until total Boc cleaving is detected. Then the mixture is extracted with ethyl acetate and water, the organic phase is dried and evaporated to dryness. The residue is recrystallised from ethyl acetate.

Yield: 300 mg (=43% of theoretical)

The representative cleaving method E was then used to synthesise Examples 13, 19, 21, 25.

D) Synthesis of Examples 26 and 27

In a pressurised reaction vessel 1.50 g (2.86 mmol) tert. butyl 4-(7-benzylamino-6-chloro-4-pyrrolidin-1-yl-pteridin-2-yl)-piperazine-1- carboxylate are placed in 3 ml dichloromethane, 20 ml dimethylamine are added while cooling with acetone/dry ice. The vessel is closed and heated to 70° C. The mixture is stirred for 48 hours under pressure. Then the reaction mixture is combined with water and extracted with ethyl acetate. The organic phase is dried and evaporated to dryness. The residue is purified by chromatography. The representative cleaving method was then used to synthesise Examples 26 and 27.

E) Representative Cleaving Method 460 mg (0.841 mmol) tert.butyl 4-(7-benzylamino-6-isobutyl-4-pyrrolidin-1-yl-pteridin-2-yl)-piperazine-1- carboxylate are placed in 10 ml dichloromethane, and 1 ml trifluoroacetic acid is added. The mixture is stirred for 16 hours at ambient temperature. Then the reaction mixture is concentrated by evaporation, the residue is extracted with dichloromethane and saturated sodium carbonate solution. The organic phase is dried and concentrated by evaporation, during which time the product crystallises out. It is suction filtered, washed and dried. Yield: 336 mg (=90% of theoretical).

F) Synthesis of Examples 32-38, Taking Example 32 as Representative a) 6-trifluoromethyl-pteridine-2,4,7-triol: 10.00 g (41.63 mmol) diaminouracil and 5.75 g (41.63 mmol) potassium carbonate are placed in 300 ml of water, then heated to 100° C. After the development of gas has ended the suspension is cooled to 60° C. and 4.25 ml (41.63 mmol) methyl 3,3,3-trifluoropyroracemate are added. The reaction mixture is stirred for 16 hours at 60° C. and for 24 hours at 100° C., then filtered while hot. The filtrate is concentrated by evaporation, the precipitate thus formed is suction filtered. This is purified by chromatography.

Yield: 3.50 g (=94% of theoretical)

b) 2,4,7-trichloro-6-trifluoromethyl-pteridine: 3.00 g (12.09 mmol) 6-trifluoromethyl-pteridine-2,4,7- triol are taken, combined with 35 ml (228.27 mmol) phosphorus oxychloride and stirred for 16 hours at 90° C. Then the excess phosphorus oxychloride is distilled off, the residue is combined with 100 ml dichloromethane and stirred for 1 hour at ambient temperature. It is filtered through silica gel, the solution is evaporated to dryness. Yield: 1.80 g (=49% of theoretical)

c) 2,7-dichloro-4-pyrrolidin-1-yl-6-trifluoromethyl-pteridine: 1.10 g (3.63 mmol) 2,4,7-trichloro-6-trifluoromethyl-pteridine are placed in 50 ml dichloromethane, then cooled to −78° C. 0.30 ml (3.63 mmol) pyrrolidine are dissolved in 10 ml dichloromethane, then slowly added dropwise. The reaction mixture is stirred for 16 hours at ambient temperature, then concentrated by evaporation. The residue is purified by chromatography.

Yield: 750 mg (=61% of theoretical)

d) Benzyl-(2-chloro-4-pyrrolidin-1-yl-6-trifluoromethyl-pteridin-7-yl)-amine: 750 mg (2.22 mmol) 2,7-dichloro-4-pyrrolidin-1-yl-6-trifluoromethyl-pteridine are dissolved in 35 ml of tetrahydrofuran and cooled to −78° C. 0.24 ml (2.22 mmol) benzylamine are placed in 15 ml of tetrahydrofuran under a nitrogen atmosphere, and slowly 1.39 ml (2.22 mmol) butyllithium are added. This solution is added dropwise to the first. Then the reaction mixture is stirred for 16 hours at ambient temperature, then concentrated by evaporation. The residue is purified by chromatography.

Yield: 650 mg (=72% of theoretical)

e) Benzyl-(2-piperazin-1-yl-4-pyrrolidin-1-yl-6-trifluoromethyl-pteridin-7-yl)-amine (Example 32): 700 mg (7.95 mmol) piperazine are placed in 24 ml dioxane and heated to 80° C. 650 mg (1.59 mmol) benzyl-(2-chloro-4-pyrrolidin-1-yl-6-trifluoromethyl-pteridin-7-yl)-amine are dissolved in 25 ml dioxane and within 0.5 hours added dropwise to the piperazine solution. Then the reaction mixture is added dropwise to 200 ml ice water, the precipitate formed is suction filtered and dried. The product still containing contaminants is purified by chromatography.

Yield: 210 mg (=29% of theoretical)

The following are a number of compounds, mentioned by way of example, which may be prepared by one of the methods of synthesis outlined above. Melting points ($m_p$) are given in ° C.

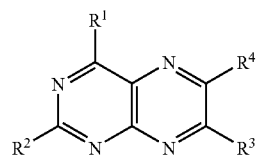

| # | $R^1$ | $R^2$ | $R^3$ | $R^4$ | $MH^+$ | $m_p$ |
|---|---|---|---|---|---|---|
| 1. | *—N(pyrrolidine) | *—N(piperazine)NH | *—NH—CH2—C6H5 | *—CH2CH3 (ethyl) | 419 | |
| 2. | *—N(pyrrolidine) | *—N(piperazine)NH | *—NH—CH2—C6H5 | *—CH(CH3)2 (isopropyl) | 433 | |

-continued

| # | R¹ | R² | R³ | R⁴ | MH⁺ | m_p |
|---|----|----|----|----|-----|-----|
| 3. | *-N(pyrrolidine) | *-N(piperazine)NH | *-NH-CH₂-phenyl | *-CH₂CH(CH₃)₂ (isobutyl) | 446 | |
| 4. | *-N(pyrrolidine) | *-N(piperazine)NH | *-NH-CH₂-phenyl | *-phenyl | 467 | |
| 5. | *-N(pyrrolidine) | *-N(piperazine)NH | *-NH-CH₂-phenyl | *-(4-F-phenyl) | 485 | 241-244 |
| 6. | *-N(pyrrolidine) | *-N(piperazine)NH | *-NH-CH₂-phenyl | *-(4-CF₃-phenyl) | 535 | 212-214 |
| 7. | *-N(pyrrolidine) | *-N(piperazine)NH | *-NH-CH₂-phenyl | *-benzo[1,3]dioxole | 511 | |
| 8. | *-N(pyrrolidine) | *-N(piperazine)NH | *-NH-CH₂-phenyl | *-(2-furyl) | 457 | |
| 9. | *-N(pyrrolidine) | *-N(piperazine)NH | *-NH-CH₂-phenyl | *-(2-thienyl) | 473 | |
| 10. | *-N(pyrrolidine) | *-N(piperazine)NH | *-NH-CH₂-phenyl | *-(benzo[b]thiophen-2-yl) | 523 | |
| 11. | *-N(pyrrolidine) | *-N(piperazine)NH | *-NH-CH₂-phenyl | *-(3-thienyl) | 473 | |
| 12. | *-N(pyrrolidine) | *-N(piperazine)NH | *-NH-CH₂-phenyl | *-(4-methylphenyl) | 481 | |
| 13. | *-N(pyrrolidine) | *-N(piperazine)NH | *-NH-CH₂-phenyl | *-N(piperidine) | 474 | |

-continued

| # | R¹ | R² | R³ | R⁴ | MH⁺ | m_p |
|---|---|---|---|---|---|---|
| 14. | pyrrolidin-1-yl | piperazin-1-yl | benzylamino | 4-chlorophenyl | 501/503 | |
| 15. | pyrrolidin-1-yl | piperazin-1-yl | benzylamino | 4-methoxyphenyl | 497 | |
| 16. | pyrrolidin-1-yl | piperazin-1-yl | benzylamino | 3,5-bis(trifluoromethyl)phenyl | 603 | 196-200 |
| 17. | pyrrolidin-1-yl | piperazin-1-yl | benzylamino | 3-cyanophenyl | 492 | |
| 18. | pyrrolidin-1-yl | piperazin-1-yl | benzylamino | 2,4,6-trimethylphenyl | 509 | 192-196 |
| 19. | pyrrolidin-1-yl | piperazin-1-yl | benzylamino | morpholin-4-yl | 476/477 | |
| 20. | pyrrolidin-1-yl | piperazin-1-yl | benzylamino | furan-3-yl | 457 | 188-192 |
| 21. | pyrrolidin-1-yl | piperazin-1-yl | benzylamino | pyrrolidin-1-yl | 460/461 | |
| 22. | pyrrolidin-1-yl | piperazin-1-yl | benzylamino | cyclopropyl | 431 | 200 |
| 23. | pyrrolidin-1-yl | piperazin-1-yl | benzylamino | cyclohexyl | 473 | 222-227 |
| 24. | pyrrolidin-1-yl | piperazin-1-yl | benzylamino | —OMe | 421 | |

-continued

| # | R¹ | R² | R³ | R⁴ | MH⁺ | m$_p$ |
|---|---|---|---|---|---|---|
| 25. | pyrrolidin-1-yl | piperazin-1-yl | NH-CH₂-phenyl | NH-phenyl | | |
| 26. | pyrrolidin-1-yl | piperazin-1-yl | NH-CH₂-phenyl | N(CH₃)₂ | 434/435 | |
| 27. | pyrrolidin-1-yl | piperazin-1-yl | NH-CH₂-phenyl | N(Et)₂ | 462/463 | |
| 28. | pyrrolidin-1-yl | Cl | NH-CH₂-cyclohexyl | piperazin-1-yl | | |
| 29. | pyrrolidin-1-yl | piperazin-1-yl | NH-CH₂-(4-Cl-phenyl) | piperazin-1-yl | | |
| 30. | pyrrolidin-1-yl | piperazin-1-yl | NH-CH₂-phenyl | —CH₃ | | |
| 31. | pyrrolidin-1-yl | 4-(N-Ph-amino)piperidin-1-yl | morpholin-4-yl | morpholin-4-yl | | |
| 32. | pyrrolidin-1-yl | piperazin-1-yl | NH-CH₂-phenyl | CF₃ | 459 | |
| 33. | pyrrolidin-1-yl | NH-CH₂-phenyl | piperazin-1-yl | CF₃ | | |
| 34. | pyrrolidin-1-yl | 4-(NMe₂)piperidin-1-yl | NH-CH₂-phenyl | CF₃ | 501 | |
| 35. | piperidin-1-yl | piperazin-1-yl | NH-CH₂-phenyl | CF₃ | 473 | |

-continued

| # | R¹ | R² | R³ | R⁴ | MH⁺ | m_p |
|---|----|----|----|----|-----|-----|
| 36. | *—N(pyrrolidine) | *—N(piperazine)NH | *—NH—CH₂—(4-F-phenyl) | CF₃ | 477 | |
| 37. | *—N(pyrrolidine) | *—N(piperazine)N-cyclopropyl | *—NH—CH₂—phenyl | CF₃ | 499 | |
| 38. | *—N(pyrrolidine) | *—N(piperazine)NH | *—S—CH₂—(4-F-phenyl) | CF₃ | 494 | |

Indications

As has been found, the compounds of formula 1 are characterised by their wide range of applications in the therapeutic field. Particular mention should be made of those applications for which the compounds according to the invention of formula 1 are preferably suited on account of their pharmaceutical efficacy as PDE4 inhibitors. Examples include respiratory or gastrointestinal diseases or complaints, inflammatory diseases of the joints, skin or eyes, cancers, and also diseases of the peripheral or central nervous system.

Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, paediatric asthma, bronchiectases, pulmonary fibrosis, ARDS (acute adult respiratory distress syndrome), bronchial oedema, pulmonary oedema, bronchitis or interstitial pneumonia or pulmonary fibrosis of various causes, such as, for example, as a result of aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Also deserving special mention is the treatment of inflammatory diseases of the gastrointestinal tract. Examples include acute or chronic inflammatory changes in gall bladder inflammation, Crohn's disease, ulcerative colitis, inflammatory pseudopolyps, juvenile polyps, colitis cystica profunda, pneumatosis cystoides interstinales, diseases of the bile duct and gall bladder, e.g. gallstones and conglomerates, for the treatment of inflammatory diseases of the joints such as rheumatoid arthritis or inflammatory diseases of the skin and eyes.

Preferential mention should also be made of the treatment of cancers. Examples include all forms of acute and chronic leukaemias such as acute lymphatic and acute myeloid leukaemia, chronic lymphatic and chronic myeloid leukaemia, and bone tumours such as osteosarcoma and all types of glioma such as oligodendroglioma and glioblastoma.

Preferential mention should also be made of the prevention and treatment of diseases of the peripheral or central nervous system. Examples of these include depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

Particularly preferably the present invention relates to the use of compounds of formula 1 for preparing a pharmaceutical composition for the treatment of inflammatory or obstructive diseases of the upper and lower respiratory tract including the lungs, such as for example allergic rhinitis, chronic rhinitis, bronchiectases, cystic fibrosis, idiopathic pulmonary fibrosis, fibrosing alveolitis, COPD, chronic bronchitis, chronic sinusitis, asthma, Crohn's disease, ulcerative colitis, particularly COPD, chronic bronchitis and asthma.

It is most preferable to use the compounds of formula 1 for the treatment of inflammatory and obstructive diseases such as COPD, chronic bronchitis, chronic sinusitis, asthma, Crohn's disease, ulcerative colitis, particularly COPD, chronic bronchitis and asthma.

It is also preferable to use the compounds of formula 1 for the treatment of diseases of the peripheral or central nervous system such as depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

An outstanding aspec of the present invention is the reduced profile of side effects. This means, within the scope of the invention, being able to administer a dose of a pharmaceutical composition without inducing vomiting, preferably nausea and most preferably malaise in the patient. It is particularly preferable to be able to administer a therapeutically effective quantity of substance without inducing emesis or nausea, at every stage of the disease.

Combinations

The compounds of formula 1 may be used on their own or in conjunction with other active substances of formula 1 according to the invention. If desired the compounds of formula 1 may also be used in combination with other pharmacologically active substances. It is preferable to use for this purpose active substances selected for example from among betamimetics, anticholinergics, corticosteroids, other PDE4-inhibitors, LTD4-antagonists, EGFR-inhibitors, dopamine agonists, H1-antihistamines, PAF-antagonists and PI3-kinase inhibitors or double or triple combinations thereof, such as for example combinations of

- betamimetics with corticosteroids, PDE4-inhibitors, EGFR-inhibitors or LTD4-antagonists,
- anticholinergics with betamimetics, corticosteroids, PDE4-inhibitors, EGFR-inhibitors or LTD4-antagonists,
- corticosteroids with PDE4-inhibitors, EGFR-inhibitors or LTD4-antagonists
- PDE4-inhibitors with EGFR-inhibitors or LTD4-antagonists
- EGFR-inhibitors with LTD4-antagonists.

The invention also encompasses combinations of three active substances, each selected from one of the above-mentioned categories of compounds.

Formulations

In another aspect the invention relates to medicaments for the treatment of respiratory complaints, which contain one or more of the above-mentioned pteridines of formula 1, which are used in combination with one or more additional active substances selected from among the betamimetics, anticholinergics, corticosteroids, PI3-kinase inhibitors, LTD4-antagonists, EGFR-inhibitors, dopamine agonists, H1-antihistamines or PAF-antagonists, preferably betamimetics, anticholinergics or corticosteroids, together or successively, for simultaneous, sequential or separate administration.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula 1 according to the preferred embodiments above.

It is particularly preferable if the compounds of formula 1 are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof. Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula 1 are administered by inhalation, particularly preferably if they are administered once or twice a day. For this purpose, the compounds of formula 1 have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula 1 are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1, 2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula 1 according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, a pteridine and one or more combination partners selected from those described above.

What is claimed is:
1. A compound of the formula 1

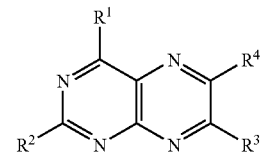

wherein
$R^1$ denotes a pyrrolidin-1-yl, piperidin-1-yl or 4-piperidinyl;
$R^2$ denotes halogen, $OR^{2.1}$, $SR^{2.1}$, $NR^{2.1}R^{2.2}$ or a group selected from among aryl, het and hetaryl, optionally substituted by a group selected from among $C_{1-6}$-alkyl, $O-C_{1-6}$-alkyl, $C_{3-6}$-cycloalkyl, $C_{7-11}$-aralkyl and $N(C_{1-4}$-alkyl$)_2$;
$R^{2.1}$ denotes H, $C_{1-4}$-alkyl, aryl or $C_{7-11}$-aralkyl;
$R^{2.2}$ denotes H, $C_{1-4}$-alkyl, aryl or $C_{7-11}$-aralkyl;
$R^3$ denotes a group of formula 1a,

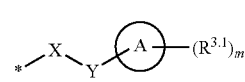

wherein
A denotes aryl or hetaryl;
X denotes $NR^{3.2}$;
Y denotes $C_{1-4}$-alkylene, optionally substituted by one or more $R^{3.3}$
m denotes 0, 1, 2 or 3;

$R^{3.1}$ each independently of one another denote $C_{1-6}$-alkyl, $C_{1-6}$-haloalkyl, $C_{1-6}$-alkyl-CONR$^{3.1.1}$R$^{3.1.2}$, —$C_{1-6}$-alkyl-NR$^{3.1.1}$R$^{3.1.2}$, OR$^{3.1.1}$, O—$C_{1-6}$-haloalkyl, NHCOR$^{3.1.1}$, SO$_2$R$^{3.1.1}$, aryl, halogen, CN, OH, CONR$^{3.1.1}$R$^{3.1.2}$; or $R^{3.1}$ together with two atoms of A forms a 5- or 6-membered carbocyclic ring or a 5- or 6-membered heterocyclic ring which optionally contains one or more oxygen or nitrogen atoms;

$R^{3.1.1}$ denotes H or $C_{1-6}$-alkyl, $R^{3.1.2}$ denotes H or $C_{1-6}$-alkyl, $R^{3.2}$ denotes H or $C_{1-6}$-alkyl;

$R^{3.3}$ each independently of one another denote $C_{1-6}$-alkyl, $C_{1-6}$-alkyl-OH, $C_{3-6}$-cycloalkyl-OH, COOR$^{3.3.1}$, CONR$^{3.3.1}$R$^{3.3.2}$; or $R^{3.3}$ together with one or two carbon atoms of Y forms a carbocyclic ring with 3, 4, 5 or 6 carbon atoms $R^{3.3.1}$ denotes H or $C_{1-6}$-alkyl;

$R^{3.3.2}$ denotes H or $C_{1-6}$-alkyl;

$R^4$ denotes a group selected from among $C_{1-6}$-alkyl, $C_{2-6}$-alkenyl, $C_{2-6}$-alkynyl, $C_{3-6}$-cycloalkyl, $C_{3-6}$-cycloalkenyl, OR$^{4.1}$, SR$^{4.1}$, $C_{1-6}$-haloalkyl, NR$^{4.1}$R$^{4.2}$ or a group selected from among aryl, het and hetaryl, optionally substituted by one or more groups selected from among $C_{1-6}$-alkyl, $C_{1-6}$-haloalkyl, CN, O—$C_{1-6}$-alkyl and halogen, $R^{4.1}$ denotes H, $C_{1-6}$-alkyl, aryl or $C_{7-11}$-aralkyl;

$R^{4.2}$ denotes H, $C_{1-6}$-alkyl, aryl or $C_{7-11}$-aralkyl;

or a pharmacologically acceptable salt thereof, wherein het or heterocyclic ring is either a five-, six- or seven-membered, saturated or unsaturated heterocyclic ring or a 5-10 membered, bicyclic heteroring which contains one, two or three heteroatoms selected from among oxygen, sulphur and nitrogen, while the ring may be linked to the molecule through a carbon or nitrogen atom and wherein hetaryl denotes five- or six-membered heterocyclic aromatic group or 5-10 membered bicyclic heteroaryl ring which contains one, two or three heteroatoms selected from among oxygen, sulphur and nitrogen and contains sufficient conjugated double bonds to form an aromatic system, while the ring may be linked to the molecule through a carbon or nitrogen atom.

2. A compound of the formula 1, according to claim 1, wherein $R^3$ denotes a group of formula 1a,

wherein

A denotes aryl or hetaryl;

X denotes NR$^{3.2}$;

Y denotes $C_{1-4}$-alkylene, optionally substituted by one or more R$^{3.3}$ m denotes 0, 1 or 2;

$R^{3.1}$ each independently of one another denote $C_{1-6}$-alkyl, $C_{1-6}$-haloalkyl, $C_{1-6}$-alkyl-CONH$_2$, —$C_{1-6}$-alkyl-NH$_2$, O—$C_{1-6}$-alkyl, O—$C_{1-6}$-haloalkyl, NHCO—$C_{1-6}$-alkyl, SO$_2$—$C_{1-6}$-alkyl, aryl, halogen, CN, OH, CONH$_2$, or $R^{3.1}$ together with two atoms of A forms a 5- or 6-membered carbocyclic ring or a 5- or 6-membered heterocyclic ring which may contain one or more oxygen or nitrogen atoms;

$R^{3.2}$ denotes H or $C_{1-6}$-alkyl;

$R^{3.3}$ each independently of one another denote $C_{1-6}$-alkyl, $C_{1-6}$-alkyl-OH, $C_{3-6}$-cycloalkyl-OH, COO—$C_{1-6}$-alkyl, COOH, CONH$_2$; or $R^{3.3}$ together with one or two carbon atoms of Y forms a carbocyclic ring with 3, 5 or 6 carbon atoms $R^4$ denotes a group selected from among $C_{1-6}$-alkyl, $C_{2-6}$-alkenyl, $C_{2-6}$-alkynyl, $C_{3-6}$-cycloalkyl, $C_{3-6}$-cycloalkenyl, O—$C_{1-6}$-alkyl, S—$C_{1-6}$-alkyl, $C_{1-6}$-haloalkyl, NR$^{4.1}$R$^{4.2}$ or a group selected from among aryl, het and hetaryl, optionally substituted by one or more groups selected from among $C_{1-6}$-alkyl, $C_{1-6}$-haloalkyl, CN, O—$C_{1-6}$-alkyl, halogen, $R^{4.1}$ denotes H or $C_{1-6}$-alkyl;

$R^{4.2}$ denotes $C_{1-6}$-alkyl or aryl;

or a pharmacologically acceptable salt thereof.

3. A compound of the formula 1 according to claim 1, wherein $R^4$ denotes $C_{3-6}$-cycloalkyl;

or a pharmacologically acceptable salt thereof.

4. A compound of the formula 1 according to claim 1, wherein $R^3$ denotes a group of formula 1a,

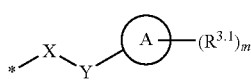

wherein

A denotes aryl or hetaryl;

X denotes NH;

Y denotes $C_{1-4}$-alkylene, optionally substituted by one or more R$^{3.3}$ m denotes 0, 1 or 2;

$R^{3.1}$ each independently of one another denote $C_{1-4}$-alkyl, $C_{1-4}$-haloalkyl, $C_{1-4}$-alkyl-CONH$_2$, $C_{1-4}$-alkyl-NH$_2$, O—$C_{1-4}$-alkyl, O—$C_{1-4}$-haloalkyl, NHCO—$C_{1-4}$-alkyl, SO$_2$—$C_{1-4}$-alkyl, halogen, CN, OH, or CONH$_2$;

$R^{3.3}$ each independently of one another denote $C_{1-4}$-alkyl, $C_{1-4}$-alkyl-OH, $C_{3-4}$-cycloalkyl-OH, COO—$C_{1-4}$-alkyl, COOH, CONH$_2$; or $R^{3.3}$ together with one or two carbon atoms of Y forms a carbocyclic ring with 3, 5 or 6 carbon atoms or a pharmacologically acceptable salt thereof.

5. A compound of the formula 1 according to claim 1, wherein $R^3$ denotes a group of formula 1a,

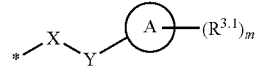

wherein

A denotes aryl or hetaryl;

X denotes NH;

Y denotes $C_{1-4}$-alkylene, optionally substituted by one or two R$^{3.3}$ m denotes 0, 1 or 2;

$R^{3.1}$ each independently of one another denote $C_{1-4}$-alkyl, $C_{1-4}$-haloalkyl, O—$C_{1-4}$-alkyl, O—$C_{1-4}$-haloalkyl, halogen, CN or OH;

$R^{3.3}$ each independently of one another denote $C_{1-4}$-alkyl, COOH or CONH$_2$; or R³·³ together with one or two carbon atoms of Y forms a carbocyclic ring with 3 carbon atoms or a pharmacologically acceptable salt thereof.

6. A compound of the formula 1 according to claim 1, wherein

R¹ denotes a group selected from among

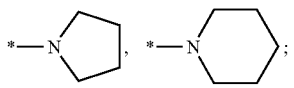

R² denotes a group selected from among chlorine,

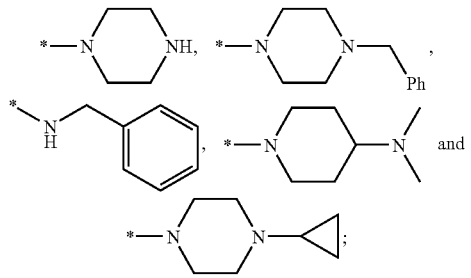

and

R³ denotes a group selected from among

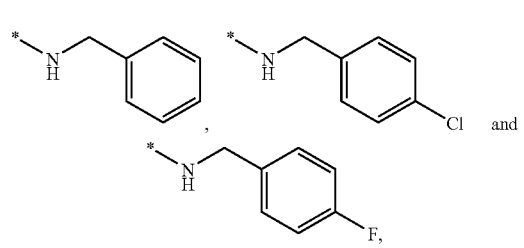

R⁴ denotes a group selected from among methyl, ethyl, propyl, 2-methylpropyl, methoxy, $CF_3$, $NMe_2$, $NEt_2$, or a pharmacologically acceptable salt thereof.

7. A pharmaceutical composition comprising a compound according to claim 1 and a pharmaceutically acceptable carrier.